US012788431B2

(12) United States Patent
Wang

(10) Patent No.: US 12,788,431 B2
(45) Date of Patent: Nov. 10, 2026

(54) NEEDLE SUPPORT STRUCTURE AND NEEDLE GUIDE BRACKET

(71) Applicant: SUZHOU LEAPMED HEALTHCARE CO., LTD., Suzhou (CN)

(72) Inventor: Qin Wang, Suzhou (CN)

(73) Assignee: Suzhou Leapmed Healthcare Co., Ltd., Suzhou (CN)

( * ) Notice: Subject to any disclaimer, the term of this patent is extended or adjusted under 35 U.S.C. 154(b) by 22 days.

(21) Appl. No.: 18/034,579

(22) PCT Filed: Nov. 5, 2020

(86) PCT No.: PCT/CN2020/126852
§ 371 (c)(1),
(2) Date: Jun. 14, 2023

(87) PCT Pub. No.: WO2022/094887
PCT Pub. Date: May 12, 2022

(65) Prior Publication Data
US 2024/0050122 A1 Feb. 15, 2024

(51) Int. Cl.
*A61B 17/34* (2006.01)
*A61B 8/00* (2006.01)

(52) U.S. Cl.
CPC ........ *A61B 17/3403* (2013.01); *A61B 8/4455* (2013.01); *A61B 2017/3405* (2013.01); *A61B 2017/3413* (2013.01)

(58) Field of Classification Search
CPC .............. A61B 17/3403; A61B 8/4455; A61B 2017/3405; A61B 2017/3413; A61B 2017/3411
See application file for complete search history.

(56) References Cited

U.S. PATENT DOCUMENTS 6,361,499 B1 3/2002 Bates
2003/0171681 A1 9/2003 Weilandt
(Continued)

FOREIGN PATENT DOCUMENTS

CN 101756715 A 6/2010
CN 104173107 A * 12/2014 ......... A61B 17/3403
(Continued)

*Primary Examiner* — Christopher Koharski
*Assistant Examiner* — Steven Malonado
(74) *Attorney, Agent, or Firm* — Sisson & Banyas, Attorneys at Law, LLC; Jeffrey J. Banyas

(57) ABSTRACT

The present invention relates to a needle support structure and a needle guide bracket, and belongs to the technical field of biopsy equipment. The needle support structure comprises a first needle inlet plate (31), a second needle inlet plate (41), and a locking device. The first plate surface of the first needle inlet plate (31) is a needle inlet wall (311). The first plate surface of the second needle inlet plate (41) is provided with a plurality of semi-open needle inlet channels (411), and the first plate surface of the second needle inlet plate (41) slots into the needle inlet wall (311) so as to form a closed needle inlet channel (411). The locking device comprises a first clamping part and a second clamping part. The first clamping part is rotatably connected to the first needle inlet plate (31), and the second clamping part is fixedly connected to the second needle inlet plate (41). Alternatively, the first clamping part is rotatably connected to the second needle inlet plate (41), and the second clamping part is fixedly connected to the first needle inlet plate (31). The first clamping part can move between a first position and a second position, thereby enabling the clamping and unclamping of the first clamping part and the second clamping part. According to the needle support structure and the needle guide bracket, the biopsy needle (300) will not be affected by an external force when released, and thus will not cause the biopsy needle (300) to move in any direction.

14 Claims, 10 Drawing Sheets

(56) References Cited

U.S. PATENT DOCUMENTS

| | | | | |
|---|---|---|---|---|
| 2006/0241477 | A1* | 10/2006 | Sasady | A61B 17/3403 600/464 |
| 2010/0168766 | A1* | 7/2010 | Zeng | A61B 17/3403 606/130 |
| 2015/0335350 | A1* | 11/2015 | Shikata | A61B 17/3403 600/443 |
| 2017/0035385 | A1* | 2/2017 | Sasady | A61B 8/0841 |

FOREIGN PATENT DOCUMENTS

| | | | | | |
|---|---|---|---|---|---|
| CN | 105902301 | A | | 8/2016 | |
| CN | 106456120 | A | | 2/2017 | |
| CN | 111297449 | A | | 6/2020 | |
| CN | 111345875 | A | * | 6/2020 | A61B 8/0841 |
| CN | 211381439 | U | * | 9/2020 | A61B 17/3403 |

* cited by examiner

NEEDLE SUPPORT STRUCTURE AND NEEDLE GUIDE BRACKET

CROSS REFERENCES AND PRIORITIES

This application claims priority from PCT Application No. PCT/CN2020/126852, filed 5 Nov. 2020.

TECHNICAL FIELD

The present invention relates to the technical field of puncture equipment, in particular to a needle support structure and a needle guide bracket.

BACKGROUND ART

The ultrasound interventional surgery is a new technology developed on the basis of ultrasound images. During surgery, it is necessary to install an ultrasound probe needle guide bracket on the ultrasound probe, and then perform puncture operations under the precise guidance of the ultrasound probe needle guide bracket. Puncture needles can directly reach lesions, and can perform surgical operations such as suction, drug administration and catheterization, or fine treatment operations such as offering microwave, radio frequency, and laser energy. The ultrasonic interventional surgery differs from the traditional surgical operation in that it can be completed only by fine needle puncture without cutting, so that a patient suffers less pain and does not need to be hospitalized, and that it is relatively safe, easy to operate, and has high practical value.

The ultrasonic probe needle guide bracket is mainly used to guide a puncture needle to reach a lesion target quickly and accurately, and has a function of quickly releasing the puncture needle after reaching the lesion tissue. That is, after the puncture needle reaches the lesion target, it is possible to separate the puncture needle from the ultrasonic probe needle guide bracket by removing the ultrasound probe and the ultrasound probe needle guide bracket separately and leaving the puncture needle in the patient's body. The effect of the ultrasound probe needle guide bracket is particularly important in the ultrasound interventional surgery, which plays a vital role in surgery efficiency, surgery success rate, and surgery safety.

At present, needle guide brackets on the market adopt a variety of different ways, including a rotating needle groove type, a clip type and the like, to achieve needle-bracket separation. Nevertheless, in practice, in the above ways, when quickly released by the doctor, the puncture needle would have a certain degree of displacement, which would affect the surgery effect and bring pain to patients.

SUMMARY OF THE INVENTION

The present invention provides a needle support structure and a needle guide bracket. When the needle support structure is separated, a first needle inlet plate and a second needle inlet plate are move away in parallel along the direction perpendicular to the needle feeding direction. This operation will not produce external forces in any direction on a puncture needle, and thus will not cause the puncture needle to produce displacement in any direction, ensuring the surgical effect of the puncture surgery, without bringing pain to patients due to the displacement of the puncture needle.

One aspect of the present invention provides a needle support structure, comprising a first needle inlet plate, a second needle inlet plate and a locking device; a first plate surface of the first needle inlet plate is a needle inlet wall; a first plate surface of the second needle inlet plate is provided with a plurality of semi-open needle inlet channels, and the needle inlet wall is fitted to the first plate surface of the second needle inlet plate to form closed needle inlet channels; the locking device comprises a first clamping part and a second clamping part; the first clamping part is rotatably connected to the first needle inlet plate, and the second clamping part is fixedly connected to the second needle inlet plate; alternatively, the first clamping part is rotatably connected to the second needle inlet plate, and the second clamping part is fixedly connected to the first needle inlet plate, wherein the first clamping part can move between a first position and a second position, thereby enabling the clamping and unclamping of the first clamping part and the second clamping part.

Alternatively, the first needle inlet plate and the second needle inlet plate are sector-shaped plates, comprising an arc-shaped end and a circle center end. First ends of the plurality of semi-open needle inlet channels are needle introduction ports, which are arranged at the arc-shaped end of the second needle inlet plate, and second ends of the plurality of semi-open needle inlet channels are communicated to form a needle release port, which is arranged at the circle center end of the second needle inlet plate.

Alternatively, the arc-shaped end of the first needle inlet plate is provided with a plurality of labels, which are located on an end face of the arc-shaped end of the first needle inlet plate and on the side of the needle introduction port. The arc-shaped end of the second needle inlet plate is provided with a handle position arm, which is perpendicular to a second plate surface of the second needle inlet plate.

Alternatively, the first clamping part comprises a rocker. The rocker comprises a rocking arm. A first end of the rocking arm is provided with a fixing hole, and a second plate surface of the first needle inlet plate is provided with a rotating boss, which is sleeved with the fixing hole. A first side end of the rocking arm is provided with a protruding positioning block, which is driven by the rocking arm to move between a first position and a second position with the rotating boss as a center of circle. The second clamping part comprises a buckle plate, which is arranged at a first side end of the second needle inlet plate. The buckle plate is perpendicular to the plane in which the second needle inlet plate is located, and the buckle plate is provided with a positioning hole. When the positioning block is located in the first position, the positioning block and the buckle plate are located on the same side of the first needle inlet plate and the second needle inlet plate, and the positioning block is clamped into the positioning hole.

Alternatively, the arc-shaped end of the first needle inlet plate is provided with a first chute along the arc-shaped surface thereof. A first positioning protrusion and a second positioning protrusion are arranged at two ends of the first chute respectively. A second end of the rocking arm is provided with a rocking block. The side of the rocking block that is fitted to the second plate surface of the first needle inlet plate is provided with a clamping opening. A positioning snap is arranged inside the clamping opening on the inner wall at the top of the clamping opening. The positioning snap is clamped into the first chute. A first positioning groove and a second positioning groove are arranged on two sides of the positioning snap respectively. When the rocking arm is in the first position, the first positioning protrusion is clamped into the first positioning groove. When the rocking arm is in the second position, the second positioning protrusion is clamped into the second positioning groove.

Alternatively, the side of the rocking block that is away from the second plate surface of the first needle inlet plate is provided with a boss and anti-slip ridges.

Alternatively, a first side end of the first needle inlet plate is provided with a first retaining wall and a second retaining wall extending in a direction away from the first needle inlet plate along a plane in which the first needle inlet plate is located, and a space is arranged between the first retaining wall and the second retaining wall, thereby forming a first notch. When the needle inlet wall of the first needle inlet plate is fitted to the first plate surface of the second needle inlet plate, the buckle plate is inserted into the first notch, and abuts against the first retaining wall and the second retaining wall.

Alternatively, the first needle inlet plate further comprises a connecting arm, which is located on a second side end of the first needle inlet plate. The plane in which the first needle inlet plate is located is perpendicular to the surface of the connecting arm, and a space is arranged between the surface of the connecting arm and the first needle inlet plate, thereby forming a second chute. A top end and a bottom end of the connecting arm are fixedly connected with an extending portion of the second side end of the first needle inlet plate respectively. The first clamping part further comprises a slider, which comprises a slider arm. A vertical arm is vertically arranged on a first plate surface of the slider arm, and the vertical arm is located in the second chute. A protruding shaft is vertically arranged on a second plate surface of the slider arm. The side of the rocking arm that is fitted to the second plate surface of the first needle inlet plate is provided with a strip-shaped third chute, in which the protruding shaft is arranged. The rocking of the rocking arm makes the third chute to drive the protruding shaft to move, so that the vertical arm moves between a first position and a second position of the second chute. The second clamping part further comprises a lock-block, which is arranged at a second side end of the second needle inlet plate. The lock-block is located in the same plane as the second needle inlet plate. The surface of the vertical arm is provided with a clip opening. The needle inlet wall is fitted to the first plate surface of the second needle inlet plate. When the vertical arm moves to the first position, the clip opening is clamped onto the lock-block.

Alternatively, a first side end of the connecting arm is provided with a stop block, which is arranged perpendicularly to the surface of the connecting arm, and which is provided with a second notch.

Another aspect of the present invention further provides a needle guide bracket, comprising the aforementioned needle support structure.

In the technical solution provided by the present invention, the first needle inlet plate and the second needle inlet plate of the needle support structure are split structures, which are connected by a locking device during the puncturing operation. When puncture needles need to be released, the locking device is unlocked to separate the first needle inlet plate from the second needle inlet plate, so that the puncture needles are separated from needle inlet channels.

During the separation operation, a first needle inlet plate and a second needle inlet plate are move away in parallel along the direction perpendicular to the needle feeding direction, which will not produce external forces in any direction on a puncture needle, and thus will not cause the movement of the puncture needle during separation operation, thereby ensuring the surgical effect of the puncture surgery, without bringing pain to patients due to the displacement of the puncture needle.

BRIEF DESCRIPTION OF THE DRAWINGS

For the purpose of illustration rather than limitation, the present invention will now be described according to its preferred embodiments, in particular with reference to the accompanying drawings, in which.

wherein:

1: body; 2: lock buckle;

11: hoop; 12: upper fixing plate; 13: lower fixing plate; 14: latch; 15: hook; 111: first positioner; 112: second positioner; 121: rotating hole; 131: rotating slot; 141: locking groove; 151: first stop plate; 152: bottom plate; 153: second stop plate; 1511: fixing groove; 1531: fourth notch; 1521: protruding surface;

21: elastic wall; 22: lock buckle post; 23: hand position; 24: fixing post; 211: rectangular hole; 241: upper rotating pin; 242: lower rotating pin; 231: second anti-slip ridge;

31: first needle inlet plate; 32: slider; 33: rocker; 34: needle groove; 311: needle inlet wall; 312: slide rail; 313: elastic snap; 314: connecting wall; 3111: rotating boss; 3112: first retaining wall; 3113: first notch; 3114: second retaining wall; 3115: first chute; 31111: elastic post; 31112: snap head; 3121: second positioning protrusion; 3122: first chute; 3123: first positioning protrusion; 3141: second notch; 3142: stop block; 3143: hanging shaft; 3116: third notch; 321: slider armarm; 3211: protruding shaft; 3212: vertical armarm; 32121: clip opening; 32122: chamfer; 331: rocking arm; 332: rocking block; 333: positioning block; 3322: boss; 3321: first anti-slip ridge; 3311: fixing hole; 3312: third chute; 3323: first positioning groove; 3324: positioning snap; 3325: second positioning groove;

41: second needle inlet plate; 42: buckle plate; 43: hand position arm; 44: lock-block; 411: needle inlet channel; 412: needle introduction port; 413: needle release port; 414: specification mark; 421: positioning hole; 422: third anti-slip ridge.

DETAILED DESCRIPTION

Figure 1:
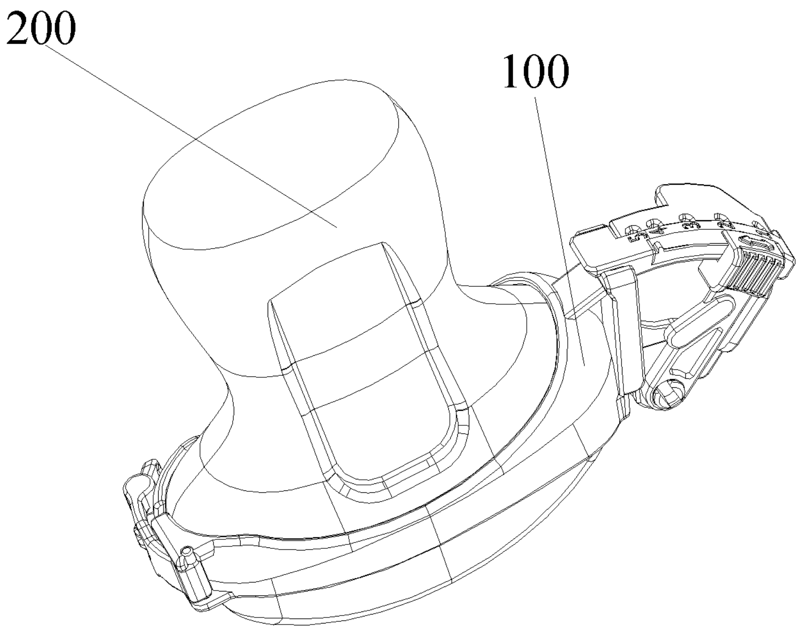
FIG. 1 is a schematic diagram of the assembly of a needle guide bracket and an ultrasonic probe according to an embodiment of the present invention.
Figure 2:
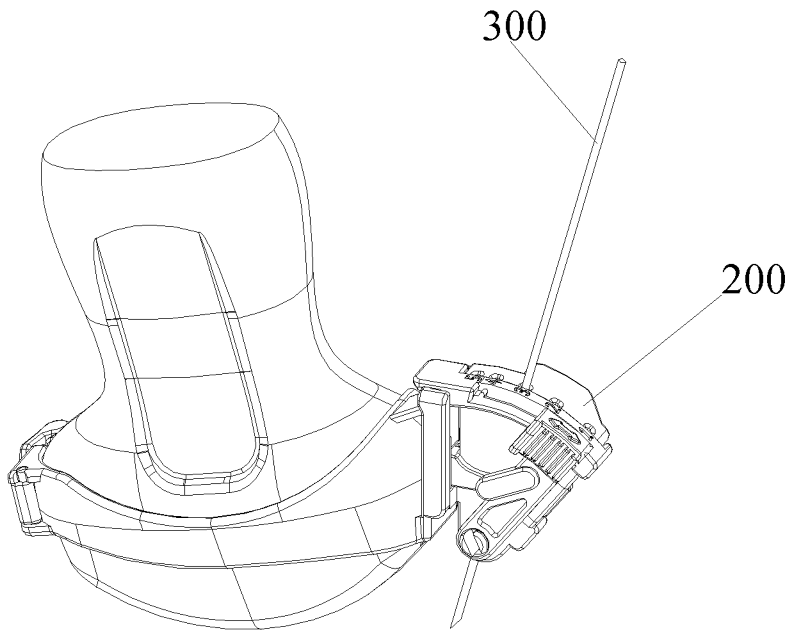
FIG. 2 is a schematic diagram of needle feeding when the needle guide bracket according to an embodiment of the present invention is in use.
Figure 3:
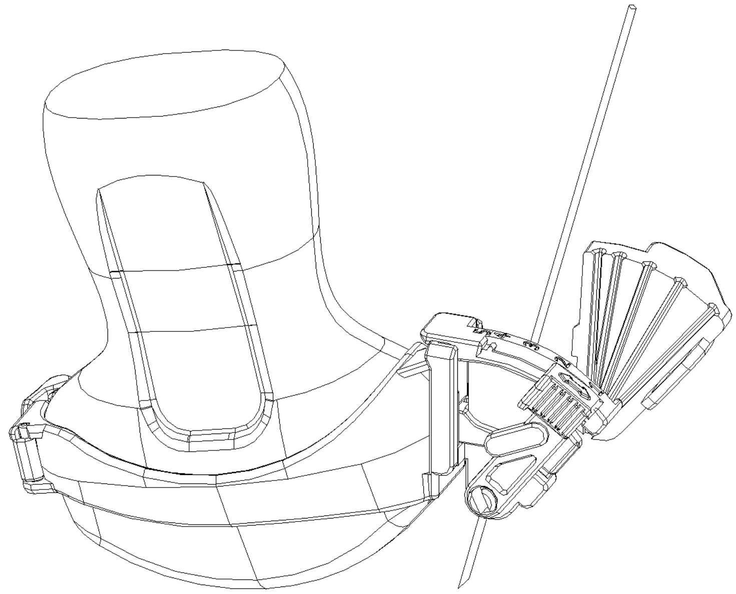
FIG. 3 is a schematic diagram of needle release when the needle guide bracket according to an embodiment of the present invention is in use.

FIG. 1 is a schematic diagram of the assembly of a needle guide bracket and an ultrasonic probe according to an embodiment of the present invention; FIG. 2 is a schematic diagram of needle inlet when the needle guide bracket according to an embodiment of the present invention is in use; and FIG. 3 is a schematic diagram of needle release when the needle guide bracket according to an embodiment of the present invention is in use. As shown in FIG. 1, before performing puncture surgery, a needle guide bracket 100 and an ultrasonic probe 200 need to be connected to form a whole, and an needle outlet end of the needle guide bracket 100 and a detection end of the ultrasonic probe 200 are located in the same direction. As shown in FIG. 2, during a needle inlet operation, a puncture needle 300 selects a corresponding needle introduction port (i.e., selecting a needle inlet angle), and then penetrates into the patient's body along a needle inlet channel. As shown in FIG. 3, when a needle release operation is required, the needle guide bracket 100 is split, thereby releasing the puncture needle 300.

Figure 4A:
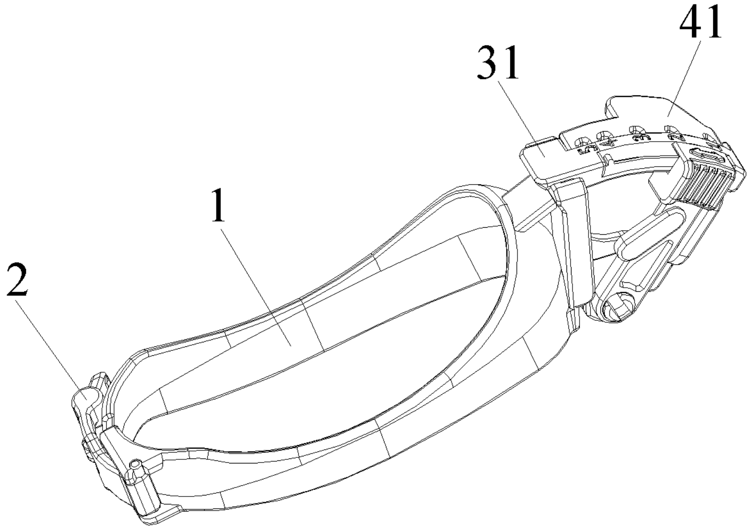
FIG. 4*a* is a structural schematic diagram of the needle guide bracket according to an embodiment of the present invention.
Figure 4B:
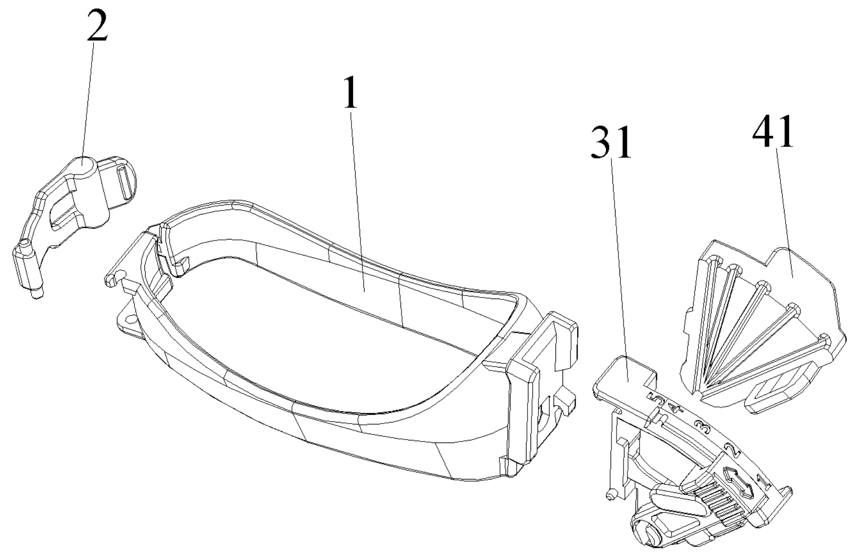
FIG. 4*b* is an exploded schematic diagram of the needle guide bracket according to an embodiment of the present invention.

FIG. 4*a* is a structural schematic diagram of the needle guide bracket according to an embodiment of the present invention, and FIG. 4*b* is an exploded schematic diagram of the needle guide bracket according to an embodiment of the present invention. As shown in FIGS. 4*a* and 4*b*, the needle guide bracket comprises a body 1, a lock buckle 2, a first needle inlet plate 3 and a second needle inlet plate 4.

Figure 5A:
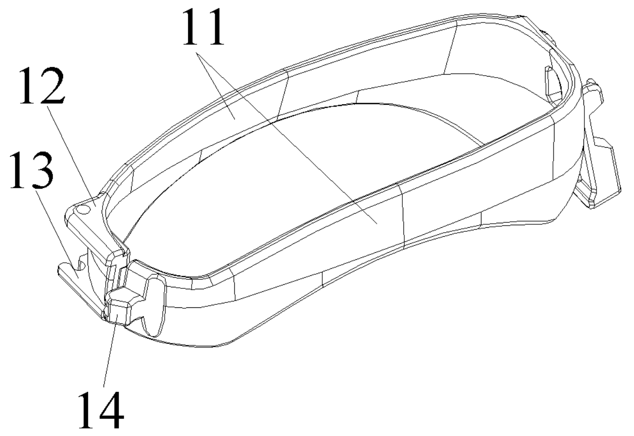
FIG. 5*a* is a structural schematic diagram of a body of the needle guide bracket according to an embodiment of the present invention.
Figure 5B:
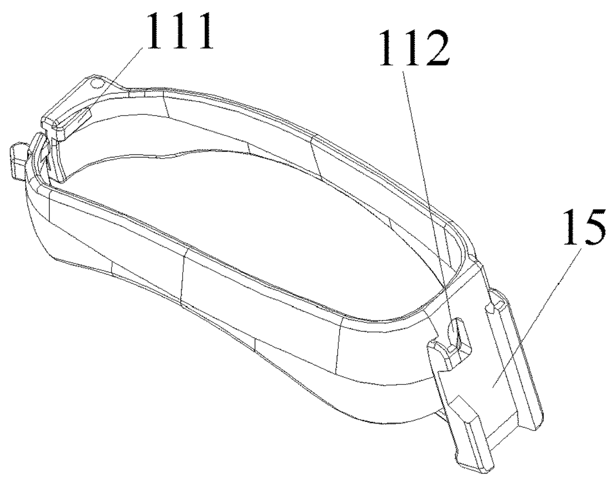
FIG. 5*b* is a structural schematic diagram of a body of the needle guide bracket according to an embodiment of the present invention from another viewing angle.

FIG. 5*a* is a structural schematic diagram of a body of the needle guide bracket according to an embodiment of the present invention, and FIG. 5*b* is a structural schematic diagram of a body of the needle guide bracket according to an embodiment of the present invention from another viewing angle. As shown in FIGS. 5*a* and 5*b*, the body 1 comprises a hoop 11, an upper fixing plate 12, a lower fixing plate 13, a latch 14 and a hook 15. The hoop 11 has a certain degree of elastic deformation ability. The hoop 11 can be opened from the notch under the action of an external force and then mounted on the ultrasonic probe, and can be snapped on the surface of the ultrasonic probe by restoring deformation after removal of the external force. By coordination of a first positioner 111 and a second positioner 112 arranged on two sides of the hoop 11 with the corresponding positioning points arranged on the ultrasonic probe, the body 1 is fitted firmly onto the surface of the ultrasonic probe. The upper fixing plate 12, the lower fixing plate 13 and the latch 14 are fixedly connected to the hoop 11 on the same side of the hoop 11, and the hook 15 is connected to the other side of the hoop 11.

Figure 6:
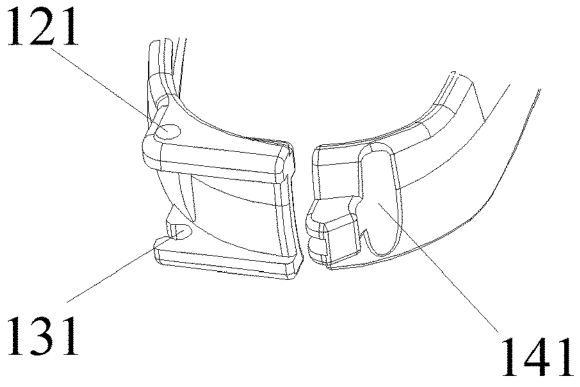
FIG. 6 is a partially enlarged diagram of a latch of the needle guide bracket according to an embodiment of the present invention.

FIG. 6 is a partially enlarged diagram of a latch of the needle guide bracket according to an embodiment of the present invention. As shown in FIGS. 5*a*, 5*b* and 6, the upper fixing plate 12 is provided with a circular rotating hole 121, the lower fixing plate 13 is provided with a rotating slot 131 with an opening, and the portion of the latch 14 that is connected to the body is provided with a locking groove 141.

Figure 7A:
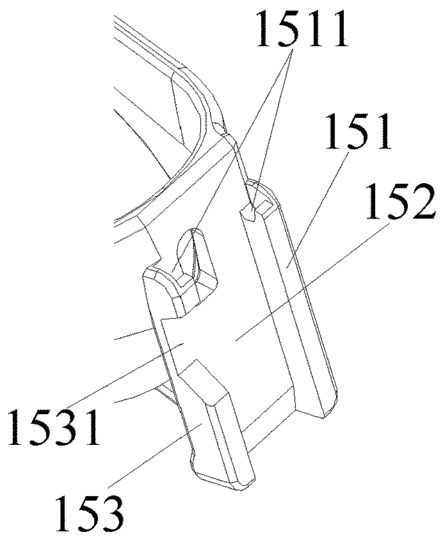
FIG. 7*a* is a partially enlarged diagram of a hook of the needle guide bracket according to an embodiment of the present invention.
Figure 7B:
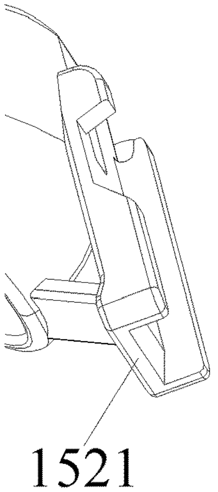
FIG. 7*b* is a partially enlarged diagram of a hook of the needle guide bracket according to an embodiment of the present invention from another viewing angle.

FIG. 7*a* is a partially enlarged diagram of a hook of the needle guide bracket according to an embodiment of the present invention, and FIG. 7*b* is a partially enlarged diagram of a hook of the needle guide bracket according to an embodiment of the present invention from another viewing angle. As shown in FIGS. 7*a* and 7*b*, the hook 15 comprises a bottom plate 152, and a first stop plate 151 and a second stop plate 153 fixedly connected to two sides of the bottom plate 152. The top ends of the first stop plate 151 and the second stop plate 153 are provided with a fixing groove 1511 respectively. The second stop plate 153 is further provided with a fourth notch 1531. A protruding surface 1521 is arranged below the bottom plate 152.

Figure 8A:
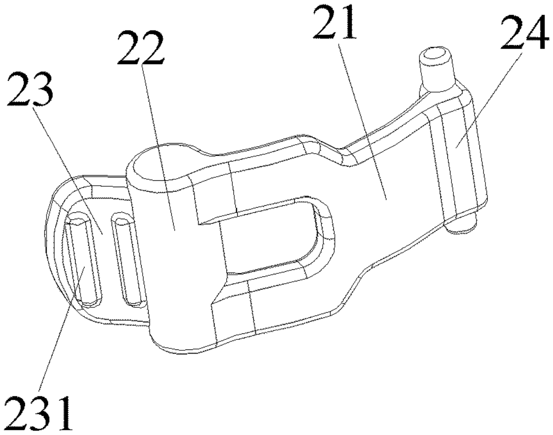
FIG. 8*a* is a structural schematic diagram of a lock buckle of the needle guide bracket according to an embodiment of the present invention.
Figure 8B:
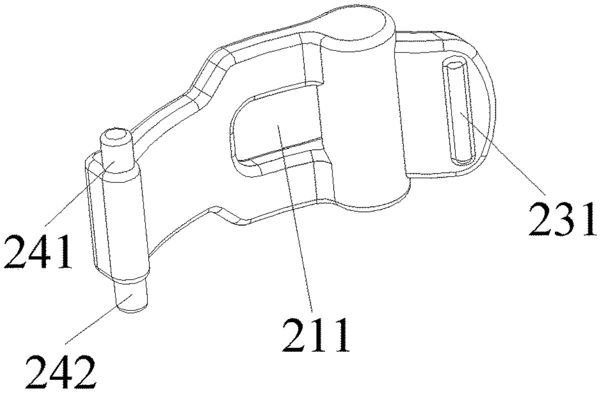
FIG. 8*b* is a structural schematic diagram of a lock buckle of the needle guide bracket according to an embodiment of the present invention from another viewing angle.

FIG. 8*a* is a structural schematic diagram of a lock buckle of the needle guide bracket according to an embodiment of the present invention, and FIG. 8*b* is a structural schematic diagram of a lock buckle of the needle guide bracket according to an embodiment of the present invention from another viewing angle. As shown in FIGS. 8*a* and 8*b*, the lock buckle 2 is integrally formed by fixedly connecting a lock buckle post 22 and a fixing post 24 through the elastic wall 21. The elastic wall 21 is of an arc-shaped structure, which has certain elastic deformation capability. The fixing post 22 is further provided with a hand position 23, which is provided with a plurality of second anti-slip ridges 231. The fixing post 24 is provided with an upper rotating pin 241 and a lower rotating pin 242 at two ends. The upper rotating pin 241 can be inserted into the rotating hole 121 of the upper fixing plate 12 arranged on the body 1, while the lower rotating pin 242 can be inserted into the rotating slot 131 of the lower fixing plate 13 arranged on the body 1, thereby realizing a movable connection between the lock buckle 2 and the body 1, and enabling the rotation of the lock buckle 2 by a certain angle around the axis position of the rotating hole 121. When the lock buckle 2 rotates to such an extent that the fixing post 22 is buckled into the locking groove 141 in the latch 14 arranged on the body 1, the hoop 11 is tightly fitted onto the surface of the ultrasonic probe by the elastic deformation capacity of the elastic wall 21 arranged on the lock buckle 2, thereby achieving a stable connection between the body 1 and the ultrasonic probe.

Figure 9:
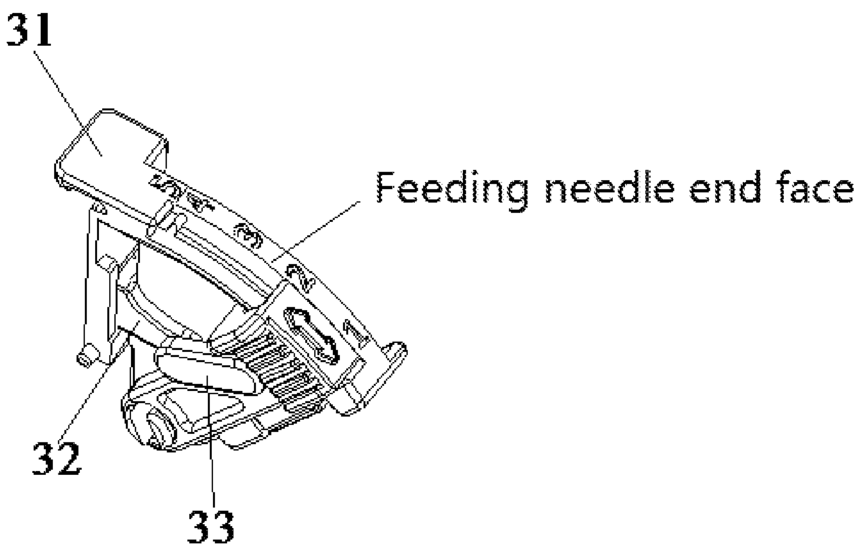
FIG. 9 is a structural schematic diagram of a first needle inlet plate in the needle support structure according to an embodiment of the present invention.

FIG. 9 is a structural schematic diagram of a first needle inlet plate in the needle support structure according to an embodiment of the present invention. As shown in FIG. 9, the needle support structure comprises a first needle inlet plate 31, a slider 32 and a rocker 33.

Figure 10A:
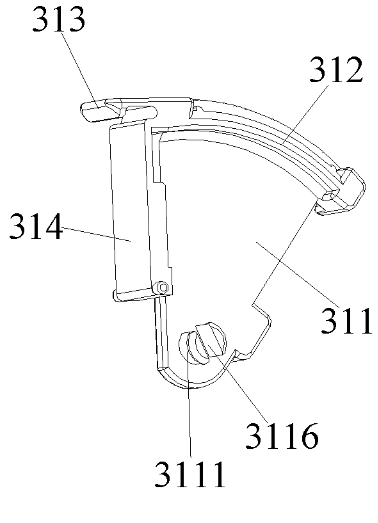
FIG. 10*a* is a structural schematic diagram of a first plate surface of the first needle inlet plate in the needle support structure according to an embodiment of the present invention.
Figure 10B:
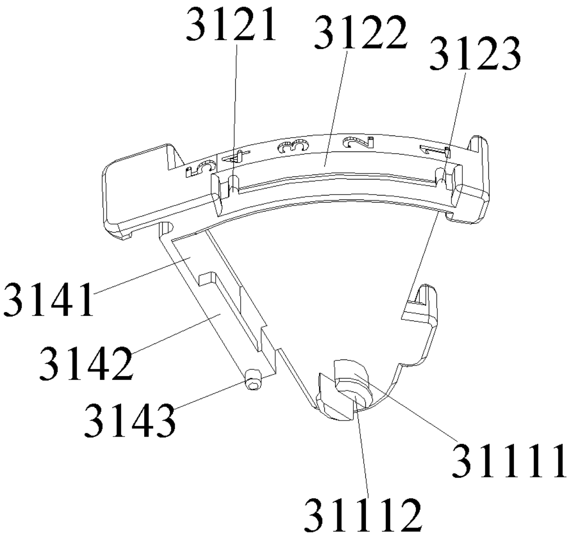
FIG. 10*b* is a structural schematic diagram of a first plate surface of the first needle inlet plate in the needle support structure according to an embodiment of the present invention from another viewing angle.
Figure 10C:
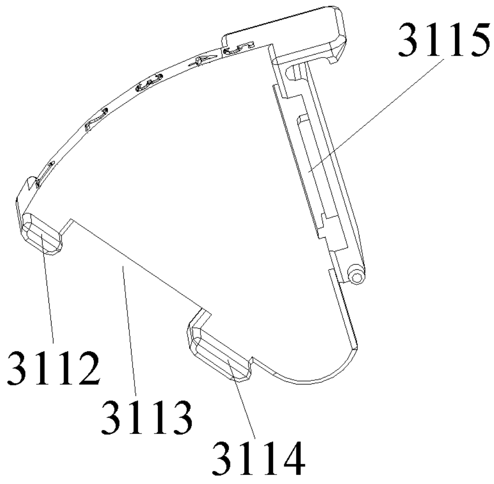
FIG. 10*c* is a structural schematic diagram of a first plate surface of the first needle inlet plate in the needle support structure according to an embodiment of the present invention from another viewing angle.

FIG. 10*a* is a structural schematic diagram of a first plate surface of the first needle inlet plate in the needle support structure according to an embodiment of the present invention; FIG. 10*b* is a structural schematic diagram of a first plate surface of the first needle inlet plate in the needle support structure according to an embodiment of the present invention from another viewing angle, and FIG. 10*c* is a structural schematic diagram of a first plate surface of the first needle inlet plate in the needle support structure according to an embodiment of the present invention from another viewing angle. As shown in FIGS. 10*a*-10*c*, the first needle inlet plate 31 is composed of a needle inlet wall 311, a slide rail 312 fixedly connected to the lower end of the needle inlet wall 311, and a connecting wall 314 fixedly connected to one side end of the needle inlet wall 311. An elastic snap 313 is fixedly connected to an end of the slide rail 312, and the base of the elastic snap 313 has a certain degree of elastic deformation ability. A first chute 3122 is arranged inside the slide rail 312, and a first positioning protrusion 3123 and a second positioning protrusion 3121 are arranged on two sides of the first chute 3122. As shown in FIG. 10*b*, the first needle inlet plate 31 is further provided with labels, such as the labels shown as numbers 1, 2, 3, 4, 5, on an end face of the arc-shaped end. When the first needle inlet plate 31 is connected to the second needle inlet plate 41, the labels are located on the side of the needle introduction port 412 of the needle inlet channel 411; and the labels play a role of identifying the needle inlet channels 411.

A rotating boss 3111 is arranged on the needle inlet wall 311. The rotating boss 3111 is fixedly connected with the needle wall 311. The middle of the rotating boss 3111 has a third notch 3116. The third notch 3116 divides the rotating boss 3111 into two parts. The rotating boss 3111 separated comprises an elastic post 31111 and a snap head 31112 arranged at an end of the elastic post 31111. A first retaining wall 3112 and a second retaining wall 3114 are further provided on an edge of the needle inlet wall 311. A first notch 3113 exists between the first retaining wall 3112 and the second retaining wall 3114.

The connecting wall 314 is provided with a hanging shaft 3143 at an end. A side end of the connecting wall 314 is further provided with a second notch 3141 and a stop block 3142. The two ends of the connecting wall 314 are fixedly connected to the needle inlet wall 311, thereby a hollow second chute 3115 is formed in the middle of the connecting wall 314.

Figure 11A:
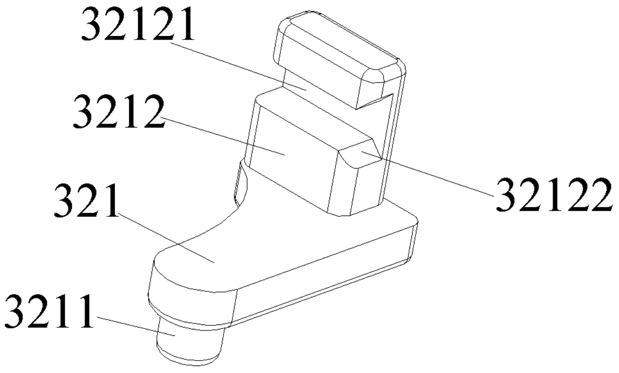
FIG. 11*a* is a structural schematic diagram of a slider in the needle support structure according to an embodiment of the present invention.
Figure 11B:
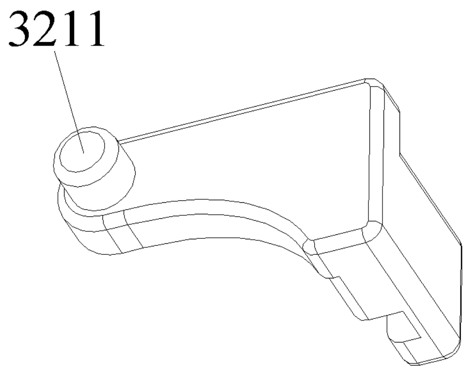
FIG. 11*b* is a structural schematic diagram of a slider in the needle support structure according to an embodiment of the present invention from another viewing angle.

FIG. 11*a* is a structural schematic diagram of a slider in the needle support structure according to an embodiment of the present invention, and FIG. 11*b* is a structural schematic diagram of a slider in the needle support structure according to an embodiment of the present invention from another viewing angle. As shown in FIGS. 11*a* and 11*b*, the slider 32 comprises a slider arm 321 and a vertical arm 3212 arranged on the slider arm 321. A protruding shaft 3211 is further arranged on the slider arm 321. The slider arm 321 is fixedly connected with the protruding shaft 3211. The protruding shaft 3211 is a cylindrical structure. The vertical arm 3212 is provided with a clip opening 32121, which is provided with a chamfer 32122 at an end.

Figure 12A:
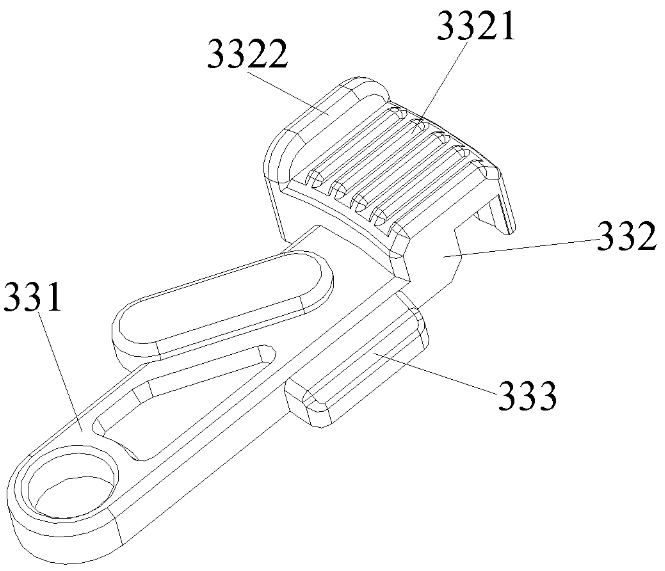
FIG. 12*a* is a structural schematic diagram of a rocker in the needle support structure according to an embodiment of the present invention.
Figure 12B:
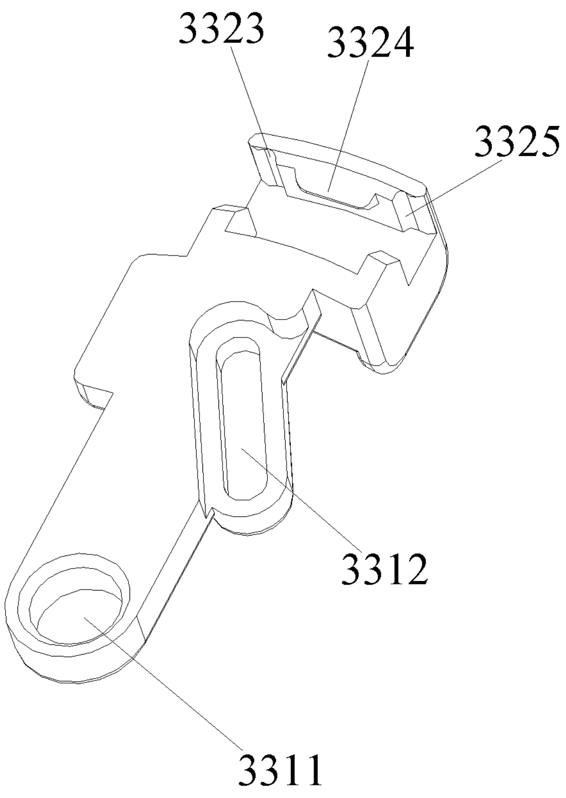
FIG. 12*b* is a structural schematic diagram of a rocker in the needle support structure according to an embodiment of the present invention from another viewing angle.

FIG. 12*a* is a structural schematic diagram of a rocker in the needle support structure according to an embodiment of the present invention, and FIG. 12*b* is a structural schematic diagram of a rocker in the needle support structure according to an embodiment of the present invention from another viewing angle. As shown in FIGS. 12*a* and 12*b*, a rocker 33 comprises a rocking arm 331 and a rocking block 332. A positioning block 333 is further arranged on a side end of the rocking arm 331. The positioning block 333 and the rocking arm 331 are fixedly connected into a whole. The rocking arm 331 is provided with a circular fixing hole 3311 at one side end thereof. The upper surface of the rocking block 332 is provided with a plurality of first anti-slip ridges 3321. A protruding boss 3322 is arranged at an end of the rocking block 332. A positioning snap 3324 is arranged on a back side of the rocking block 332. A first positioning groove 3323 and a second positioning groove 3325 are arranged on two sides of the positioning snap 3324 respectively.

Figure 13A:
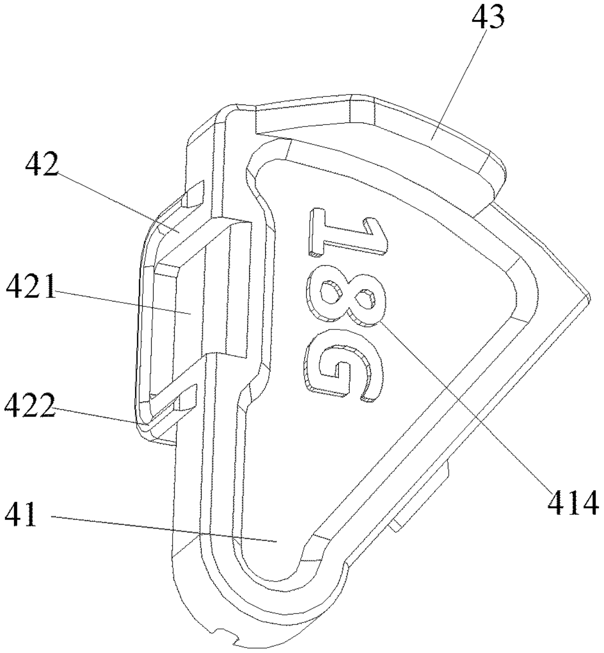
FIG. 13*a* is a structural schematic diagram of a second needle inlet plate in the needle support structure according to an embodiment of the present invention.
Figure 13B:
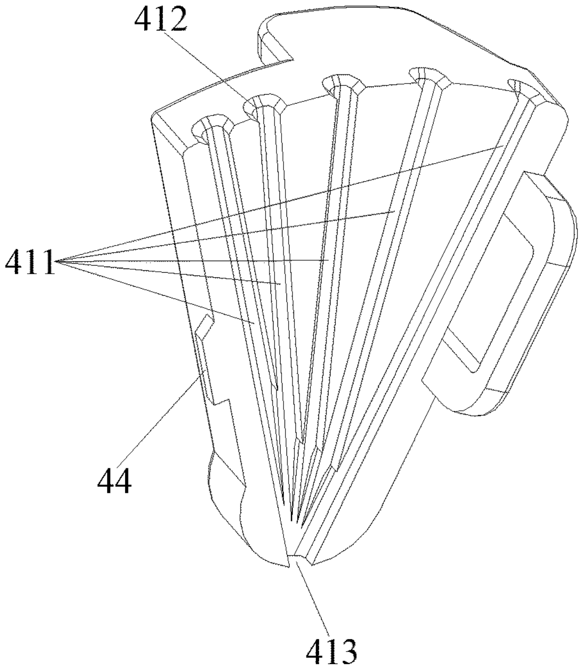
FIG. 13*b* is a structural schematic diagram of a second needle inlet plate in the needle support structure according to an embodiment of the present invention from another viewing angle.

FIG. 13*a* is a structural schematic diagram of a second needle inlet plate in the needle support structure according to an embodiment of the present invention, and FIG. 13*b* is a structural schematic diagram of a second needle inlet plate in the needle support structure according to an embodiment of the present invention from another viewing angle. As shown in FIGS. 13*a* and 13*b*, the second needle inlet plate 41 is fixedly connected to a buckle plate 42 and a hand position arm 43. A lock-block 44 is arranged on the second needle inlet plate 41, and is fixedly connected with the second needle inlet plate 41. The buckle plate 42 is provided with a third anti-slip ridge 422, which can prevent slipping when the second needle inlet plate 41 is taken out. The second needle inlet plate 41 is provided with a specification mark 414 on the upper surface, which can clearly display specifications and sizes of the puncture needles or biopsy needles that the second needle inlet plate 41 can adapt to. The second needle inlet plate 41 is provided with a plurality of semi-open needle inlet channels 411 on the lower surface, which can be set to different specifications and sizes in order to adapt to the channel of puncture needles of different specifications. A top end of the needle inlet channel 411 is provided with a needle introduction port 412, which can facilitate a surgeon to rapidly insert a puncture needle into the needle inlet channel 411. The size of the needle inlet channel 411 corresponds to the specification mark 414, so the second needle inlet plate 41 has a plurality of models with different specifications.

In the embodiments of the present invention, the first clamping part and the second clamping part include two snap-on connections between them, one is the clamping connection between the positioning block 333 and the positioning hole 421, and the other is the clamping connection between the vertical arm 3212 and the lock-block 44, wherein the connection or separation in the two snap-on connections can be achieved at the same time through the swing of the rocker 33.

In the embodiments of the present invention, the assembling relations among individual parts mentioned above are as follows.

The slider 32 can enter the second chute 3115 by passing through the second notch 3141 arranged on the first needle inlet plate 31. The slider 32 can slide back and forth within the second chute 3115 along the length direction of the second chute 3115, and the stop block 3142 can prevent the slider 32 from falling out of the second chute 3115 when sliding within the second chute 3115.

The fixing hole 3311 in the rocker 33 can be sleeved onto the rotating boss 3111 arranged on the first needle inlet plate 31 under the press of an external force. The elastic post 31111 will be deformed toward the third notch 3116 when pressed, thereby smoothly pressing the rotating boss 3111 into the fixing hole 3311. After the rotating boss is pressed in place, the elastic post 31111 returns to its position, and the snaphead 31112 makes the fixing hole 3311 of the rocker 33 connected fixedly to the first needle inlet plate 31. The rocking block 332 of the rocker 33 is snapped into the first chute 3122 arranged on the first needle inlet plate 31 by the positioning snap 3324. In this case, two ends of the rocker 33 are movably connected with the first needle inlet plate 31, and the rocker 33 can rotate and move around the axis position of the rotating boss 3111.

After the slider 32 is mounted in the second chute 3115 arranged on the first needle inlet plate 31, the protruding shaft 3211 arranged on the slider 32 can be inserted into the third chute 3312 arranged on the rocker 33. The protruding shaft 3211 can slide in the third chute 3312. When the rocker 33 rotatably swings on the first needle inlet plate 31, the protruding shaft 3211 is driven by the third chute 3312 to slide within the third chute 3312, so that the slider 32 can be driven to move a certain distance in the second chute 3115 arranged on the first needle inlet plate 31 along the length direction of the second chute 3115.

The assembled first needle inlet plate 31 is assembled with the fixing groove 1511 arranged on the body 1 by the hanging shaft 3143 on the first needle inlet plate 31, and the circular hanging shaft 3143 can rotate around the fixing groove 1511 to a certain extent after being assembled into the fixing groove 1511. The first needle inlet plate 31 is rotated, so that the connecting wall 314 arranged on the first needle inlet plate 31 is snapped on the bottom plate 152 of the body 1, and thus the elastic snap 313, after being deformed, is buckled on the protruding surface 1521 arranged on the body 1, so that the first needle inlet plate 31 is stably mounted on the body 1.

When the first needle inlet plate 31 and the second needle inlet plate 41 are connected, the second needle inlet plate 41 is fitted to the first needle inlet plate 31 by inserting the buckle plate 42 into the first notch 3113 arranged on the first needle inlet plate 31, so that the semi-open needle inlet channels 411 constitutes closed needle inlet channels. The first retaining wall 3112, the second retaining wall 3114 and the connecting wall 314 arranged on the first needle inlet plate 31 can position the location of the second needle inlet plate 41, so that the second needle inlet plate 41 does not move relative to the first needle inlet plate 31 after being loaded into the first needle inlet plate 31.

After the connection between the first needle inlet plate 31 and the second needle inlet plate 41 is completed, the rocker 33 is swung towards the direction of the first positioning protrusion 3123 arranged on the first needle inlet plate 31 by being toggled. When the second positioning groove 3325 arranged on the rocker 33 falls into the first positioning protrusion 3123 arranged on the first needle inlet plate 31, the positioning block 333 arranged on the rocker 33 is inserted into the positioning hole 421 arranged in the second needle inlet plate 41; at the same time, by swinging, the rocker 33 can drive the slider 32 to move, so that the lock-block 44 arranged on the second needle inlet plate 41 is smoothly clipped into the clip opening 32121 arranged on the slider 32, thereby firmly locking the two side ends of the second needle inlet plate 41 on the first needle inlet plate 31. In this case, the semi-open needle inlet channel 411 arranged in the second needle inlet plate 41 is fitted to the first needle inlet plate 31 to form a closed needle inlet channel, through which a puncture needle or a biopsy needle having corresponding specification can pass. In this state, the aforementioned parts are located at the first position, that is, the current positions of the positioning block 333, the slider 32, the vertical arm 32121 and the like are their first positions.

In the same way, when the rocker 33 is pushed reversely to swing towards the direction of the second positioning protrusion 3121 arranged on the first needle inlet plate 31, the rocker 33 will drive the positioning block 333 to leave the positioning hole 421 arranged in the second needle inlet plate 41; at the same time, the rocker 33 also drives the slider 32 to move, so that the clip opening 32121 arranged on the slider 32 leaves the lock-block 44 arranged on the second needle inlet plate 41. When the first positioning groove 3323 arranged on the rocker 33 falls into the second positioning protrusion 3121 arranged on the first needle inlet plate 31, the second needle inlet plate 41 can be horizontally moved away by pinching with hand the hand position arm 43 arranged on the second needle inlet plate 41, thereby achieving the function of separating a needle from a needle guide bracket. In this state, the aforementioned parts are in the second position, that is, the positioning block 333, the slider 32, the vertical arm 32121 and the like are moved in the reverse direction with the swing of the rocker 33, i.e. from the first position to the second position thereof.

The aforementioned specific embodiments do not constitute a limitation on the scope of protection of the present invention. It should be understood by those skilled in the art that various modifications, combinations, sub-combinations and substitutions may occur depending on design requirements and other factors. Any modifications, equivalent substitutions and improvements made within the spirit and principle of the present invention should be included within the scope of protection of the present invention.

The invention claimed is:

1. A needle support structure, comprising a first needle inlet plate (31), a second needle inlet plate (41) and a locking device, wherein a first plate surface of the first needle inlet plate (31) is a needle inlet wall (311); wherein a first plate surface of the second needle inlet plate (41) is provided with a plurality of semi-open needle inlet channels (411), and the needle inlet wall (311) is fitted to the first plate surface of the second needle inlet plate (41) to form closed needle channels;

the locking device comprises a first clamping part and a second clamping part, wherein the first clamping part comprises a rocker (33), which comprises a rocking arm (331), and a first end of the rocking arm (331) is rotatably connected to the first needle inlet plate (31), and the second clamping part is fixedly connected to the second needle inlet plate (41); a first side end of the rocking arm (331) is provided with a protruding positioning block (333); the second clamping part comprises a buckle plate (42), which is arranged on a first side end of the second needle inlet plate (41), is perpendicular to a plane in which the second needle inlet plate is located, and the buckle plate is provided with a positioning hole (421); when the protruding positioning block (333) is in a first position, the protruding positioning block (333) and the buckle plate (42) are located on a same side of the first needle inlet plate (31) and the second needle inlet plate (41), and the protruding positioning block (333) is clamped into the positioning hole (4211);

wherein the first needle inlet plate (31) is provided with a rotating boss (3111) having an elastic structure, the rotating boss (3111) comprising an elastic post (31111) and a snap head (31112) arranged at an end of the elastic post (31111), and a third notch (3116) adjacent to the elastic post (31111) that allows elastic deformation of the elastic post (31111); the first end of the rocking arm (331) is provided with a fixing hole (3311), and the rotating boss (3111) is elastically snapped into the fixing hole (3311) with the snap head (31112) locking the rocking arm (331) on the rotating boss (3111);

the first clamping part further comprises a slider (32), which comprises a slider arm (321); a vertical arm (3212) vertically arranged on a first plate surface of the slider arm (321); the second clamping part further comprises a lock-block (44), which is arranged on a second side end of the second needle inlet plate (41), and which is located in the plane in which the second needle inlet plate is located; a surface of the vertical arm (3212) is provided with a clip opening (32121), the needle inlet wall (311) is fitted to the first plate surface of the second needle inlet plate (41), and when the vertical arm (3212) moves to the first position, the clip opening (32121) is clamped onto the lock-block (44); wherein the first clamping part can move between a first clamping part position and a second clamping part position, thereby enabling two snap-on connections between the first clamping part and the second clamping part, the two snap-on connections each comprises:

in the first position, the positioning block (333) on the first side end of the rocking arm (331) is clamped into the positioning hole (421) of the buckle plate (42); with the clip opening (32121) of the vertical arm (3212) is clamped onto the lock-block (44);

in the second position, the positioning block (333) is disengaged from the positioning hole (421), and the clip opening (32121) of the vertical arm (3212) is disengaged from the lock-block (44), so that the first needle inlet plate (31) and the second needle inlet plate (41) are separated by translating in a direction perpendicular to an insertion direction of a puncture needle;

wherein the first end of the rocking arm (331) is provided with the fixing hole (3311), and a second plate surface of the first needle inlet plate (31) is provided with the rotating boss (3111) which is sleeved with the fixing hole (3311); wherein the protruding positioning block (333) is driven by the rocking arm (331) to move between the first position and the second position with the rotating boss (3111) as a center of circle;

wherein the first needle inlet plate (31) further comprises a connecting arm (314), which is located on a second side end of the first needle inlet plate (31);

wherein the plane in which the first needle inlet plate (31) is located is perpendicular to a surface of the connecting arm (314), and a space is arranged between the surface of the connecting arm (314) and the first needle inlet plate (31), thereby forming a second chute (3115), a top end and a bottom end of the connecting arm (314) being fixedly connected with an extending portion of the second side end of the first needle inlet plate (31) respectively;

wherein the vertical arm (3212) is located in the second chute (3115); a protruding shaft (3211) is vertically arranged on a second plate surface of the slider arm (321); a side of the rocking arm (331) that is fitted to the second plate surface of the first needle inlet plate (31) is provided with a strip-shaped third chute (3312), in which the protruding shaft (3211) is arranged; a rocking of the rocking arm (331) makes the strip-shaped third chute (3312)) drive the protruding shaft (3211) to move, so that the vertical arm (3212) moves between the first position and a second position of the second chute (3115).

2. The needle support structure according to claim 1, wherein the first needle inlet plate (31) and the second needle inlet plate (41) are sector-shaped plates, comprising an arc-shaped end and a circle center end;

wherein first ends of the plurality of semi-open needle inlet channels (411) are a plurality of needle introduction ports (412), which are arranged at the arc-shaped end of the second needle inlet plate (41), and second ends of the plurality of semi-open needle inlet channels are communicated to form a needle release port (413), which is arranged at the circle center end of the second needle inlet plate (41).

3. The needle support structure according to claim 2, wherein the arc-shaped end of the first needle inlet plate (31) is provided with a plurality of labels, which are located on an end face of the arc-shaped end of the first needle inlet plate (31) and on a side of at least one of the needle introduction ports (412);

wherein the arc-shaped end of the second needle inlet plate (41) is provided with a hand position arm (43), which is perpendicular to a second plate surface of the second needle inlet plate (41).

4. The needle support structure according to claim 3, wherein the arc-shaped end of the first needle inlet plate (31) is provided with a first chute (3122) along an arc-shaped surface thereof, and a first positioning protrusion (3123) and a second positioning protrusion (3121) are arranged at two ends of the first chute (3122) respectively; a second end of the rocking arm (331) is provided with a rocking block (332), wherein a side of the rocking block (332) that is fitted to the second plate surface of the first needle inlet plate (31) is provided with a clamping opening, in which a positioning snap (3324) is provided on an inner wall at a top thereof; the positioning snap (3324) is clamped into the first chute (3122), and a first positioning groove (3323) and a second positioning groove (3325) are arranged at two sides of the positioning snap (3324) respectively; when the rocking arm (331) is in the first position, the first positioning protrusion (3123) is clamped into the first positioning groove (3323), and when the rocking arm (331) is in the second position, the second positioning protrusion (3121) is clamped into the second positioning groove (3325).

5. The needle support structure according to claim 4, wherein the side of the rocking block (332) that is away from the second plate surface of the first needle inlet plate (31) is provided with a boss (3322) and first anti-slip ridges (3321).

6. The needle support structure according to claim 3, wherein a first side end of the first needle inlet plate (31) is provided with a first retaining wall (3112) and a second retaining wall (3114) extending in a direction away from the first needle inlet plate (31) along the plane in which the first needle inlet plate (31) is located, and a space is arranged between the first retaining wall (3112) and the second retaining wall (3114) to form a first notch (3113); wherein when the needle inlet wall (311) of the first needle inlet plate (31) is fitted to the first plate surface of the second needle inlet plate (41), the buckle plate (42) is inserted into the first notch (3113), and abuts against the first retaining wall (3112) and the second retaining wall (3114).

7. The needle support structure according to claim 5, wherein a first side end of a connecting arm (314) is provided with a stop block (3142), which is arranged vertically on the surface of the connecting arm (314), and which is provided with a second notch (3141).

8. A needle guide bracket, comprising a needle support structure comprising a first needle inlet plate (31), a second needle inlet plate (41) and a locking device, wherein a first plate surface of the first needle inlet plate (31) is a needle inlet wall (311);

wherein a first plate surface of the second needle inlet plate (41) is provided with a plurality of semi-open needle inlet channels (411), and the needle inlet wall (311) is fitted to the first plate surface of the second needle inlet plate (41) to form closed needle channels;

the locking device comprises a first clamping part and a second clamping part, wherein the first clamping part comprises a rocker (33), which comprises a rocking arm (331), and a first end of the rocking arm (331) is rotatably connected to the first needle inlet plate (31), and the second clamping part is fixedly connected to the second needle inlet plate (41); a first side end of the rocking arm (331) is provided with a protruding positioning block (333); the second clamping part comprises a buckle plate (42), which is arranged on a first side end of the second needle inlet plate (41), is perpendicular to a plane in which the second needle inlet plate is located, and the buckle plate is provided with a positioning hole (421); when the protruding positioning block (333) is in a first position, the protruding positioning block (333) and the buckle plate (42) are located on a same side of the first needle inlet plate (31) and the second needle inlet plate (41), and the protruding positioning block (333) is clamped into the positioning hole (421);

wherein the first needle inlet plate (31) is provided with a rotating boss (3111) having an elastic structure, the rotating boss (3111) comprising an elastic post (31111) and a snap head (31112) arranged at an end of the elastic post (31111), and a third notch (3116) adjacent to the elastic post (31111) that allows elastic deformation of the elastic post (31111); the first end of the rocking arm (331) is provided with a fixing hole (3311), and the rotating boss (3111) is elastically snapped into the fixing hole (3311) with the snap head (31112) locking the rocking arm (331) on the rotating boss (3111);

the first clamping part further comprises a slider (32), which comprises a slider arm (321); a vertical arm (3212) vertically arranged on a first plate surface of the slider arm (321); the second clamping part further comprises a lock-block (44), which is arranged on a second side end of the second needle inlet plate (41), and which is located in the plane in which the second needle inlet plate is located; a surface of the vertical arm (3212) is provided with a clip opening (32121), the needle inlet wall (311) is fitted to the first plate surface of the second needle inlet plate (41), and when the vertical arm (3212) moves to the first position, the clip opening (32121) is clamped onto the lock-block (44);

wherein the first clamping part can move between a first clamping part position and a second clamping part position, thereby enabling two snap-on connections between the first clamping part and the second clamping part, the two snap-on connections each comprises:

in the first position, the positioning block (333) on the first side end of the rocking arm (331) is clamped into the positioning hole (421) of the buckle plate (42); with the clip opening (32121) of the vertical arm (3212) is clamped onto the lock-block (44);

in the second position, the positioning block (333) is disengaged from the positioning hole (421), and the clip opening (32121) of the vertical arm (3212) is disengaged from the lock-block (44), so that the first needle inlet plate (31) and the second needle inlet plate (41) are separated by translating in a direction perpendicular to an insertion direction of a puncture needle;

wherein the first end of the rocking arm (331) is provided with the fixing hole (3311), and a second plate surface of the first needle inlet plate (31) is provided with the rotating boss (3111) which is sleeved with the fixing hole (3311); wherein the protruding positioning block (333) is driven by the rocking arm (331) to move between the first position and the second position with the rotating boss (3111) as a center of circle;

wherein the first needle inlet plate (31) further comprises a connecting arm (314), which is located on a second side end of the first needle inlet plate (31);

wherein the plane in which the first needle inlet plate (31) is located is perpendicular to a surface of the connecting arm (314), and a space is arranged between the surface of the connecting arm (314) and the first needle inlet plate (31), thereby forming a second chute (3115), a top end and a bottom end of the connecting arm (314) being fixedly connected with an extending portion of the second side end of the first needle inlet plate (31) respectively;

wherein the vertical arm (3212) is located in the second chute (3115); a protruding shaft (3211) is vertically arranged on a second plate surface of the slider arm (321); a side of the rocking arm (331) that is fitted to the second plate surface of the first needle inlet plate (31) is provided with a strip-shaped third chute (3312), in which the protruding shaft (3211) is arranged; a rocking of the rocking arm (331) makes the strip-shaped third chute (3312)) drive the protruding shaft (3211) to move, so that the vertical arm (3212) moves between the first position and a second position of the second chute (3115).

9. The needle guide bracket according to claim 8, wherein the first needle inlet plate (31) and the second needle inlet plate (41) are sector-shaped plates, comprising an arc-shaped end and a circle center end;

wherein first ends of the plurality of semi-open needle inlet channels (411) are a plurality of needle introduction ports (412), which are arranged at the arc-shaped end of the second needle inlet plate (41), and second ends of the plurality of semi-open needle inlet channels are communicated to form a needle release port (413), which is arranged at the circle center end of the second needle inlet plate (41).

10. The needle guide bracket according to claim 9, wherein the arc-shaped end of the first needle inlet plate (31) is provided with a plurality of labels, which are located on an end face of the arc-shaped end of the first needle inlet plate (31) and on a side of the at least one of the needle introduction ports (412);

wherein the arc-shaped end of the second needle inlet plate (41) is provided with a hand position arm (43), which is perpendicular to a second plate surface of the second needle inlet plate (41).

11. The needle guide bracket according to claim 10, wherein the arc-shaped end of the first needle inlet plate (31) is provided with a first chute (3122) along an arc-shaped surface thereof, and a first positioning protrusion (3123) and a second positioning protrusion (3121) are arranged at two ends of the first chute (3122) respectively; a second end of the rocking arm (331) is provided with a rocking block (332), wherein a side of the rocking block (332) that is fitted to the second plate surface of the first needle inlet plate (31) is provided with a clamping opening, in which a positioning snap (3324) is provided on an inner wall at a top thereof; the positioning snap (3324) is clamped into the first chute (3122), and a first positioning groove (3323) and a second positioning groove (3325) are arranged at two sides of the positioning snap (3324) respectively; when the rocking arm (331) is in the first position, the first positioning protrusion (3123) is clamped into the first positioning groove (3323), and when the rocking arm (331) is in the second position, the second positioning protrusion (3121) is clamped into the second positioning groove (3325).

12. The needle guide bracket according to claim 11, wherein the side of the rocking block (332) that is away from the second plate surface of the first needle inlet plate (31) is provided with a boss (3322) and first anti-slip ridges (3321).

13. The needle guide bracket according to claim 10, wherein a first side end of the first needle inlet plate (31) is provided with a first retaining wall (3112) and a second retaining wall (3114) extending in a direction away from the first needle inlet plate (31) along the plane in which the first needle inlet plate (31) is located, and a space is arranged between the first retaining wall (3112) and the second retaining wall (3114) to form a first notch (3113); wherein when the needle inlet wall (311) of the first needle inlet plate (31) is fitted to the first plate surface of the second needle inlet plate (41), the buckle plate (42) is inserted into the first notch (3113), and abuts against the first retaining wall (3112) and the second retaining wall (3114).

14. The needle guide bracket according to claim 12, wherein a first side end of a connecting arm (314) is provided with a stop block (3142), which is arranged vertically on the surface of the connecting arm (314), and which is provided with a second notch (3141).

* * * * *